United States Patent [19]

Sutter

[11] Patent Number: 5,668,577

[45] Date of Patent: Sep. 16, 1997

[54] VIDEO CIRCUIT FOR GENERATING SPECIAL FAST DYNAMIC DISPLAYS

[76] Inventor: Erich E. Sutter, 711 Palomar Dr., Redwood City, Calif. 94062

[21] Appl. No.: 289,645

[22] Filed: Aug. 12, 1994

[51] Int. Cl.$^6$ .................................................. G09G 5/00
[52] U.S. Cl. ................................... 345/197; 345/200
[58] Field of Search ................................. 345/189, 190, 345/191, 187, 197, 198, 199, 200, 147

[56] References Cited

U.S. PATENT DOCUMENTS

| | | | |
|---|---|---|---|
| 3,701,988 | 10/1972 | Allaart | 345/197 |
| 3,836,902 | 9/1974 | Okuda et al. | 345/197 |
| 5,359,342 | 10/1994 | Nakai et al. | 345/147 |

Primary Examiner—Richard Hjerpe
Assistant Examiner—Regina Liang
Attorney, Agent, or Firm—David Pressman

[57] ABSTRACT

A circuit is provided for generating fast dynamic video displays on a screen containing an arbitrary number of areas of any shape and size is. The screen areas are independently modulated in time in accordance with binary m-sequences and other Hadamard sets. The circuit comprises a number of 1-bit video planes (34) and a circuit for selecting specific video planes and a circuit (38) generating the modulo two sum of the content of a selected number of these planes. The selected video planes are identified by the ONEs in a binary word transferred to a register (36) of the circuit by a processor (14). Programming code is provided for the generation of sequences of such words that effect temporal modulation of screen areas in accordance with binary m-sequences or other Hadamard sets. Programming code is also provided for loading the screen areas that effect a predetermined advance in the m-sequence modulation from one area to the next and permitting different choices of the states of modulation in each screen area.

14 Claims, 4 Drawing Sheets

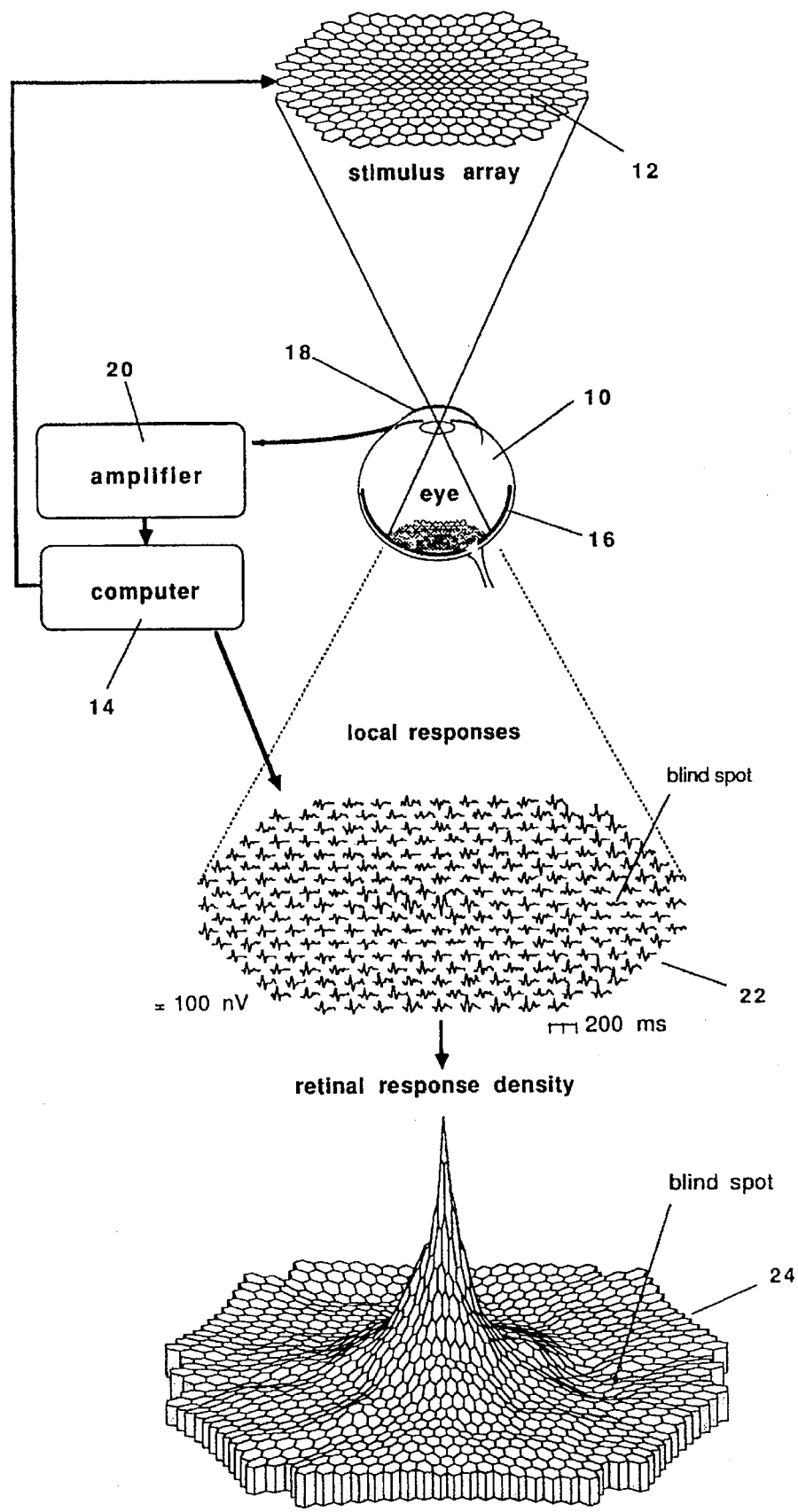
Fig. 1 --- Prior Art

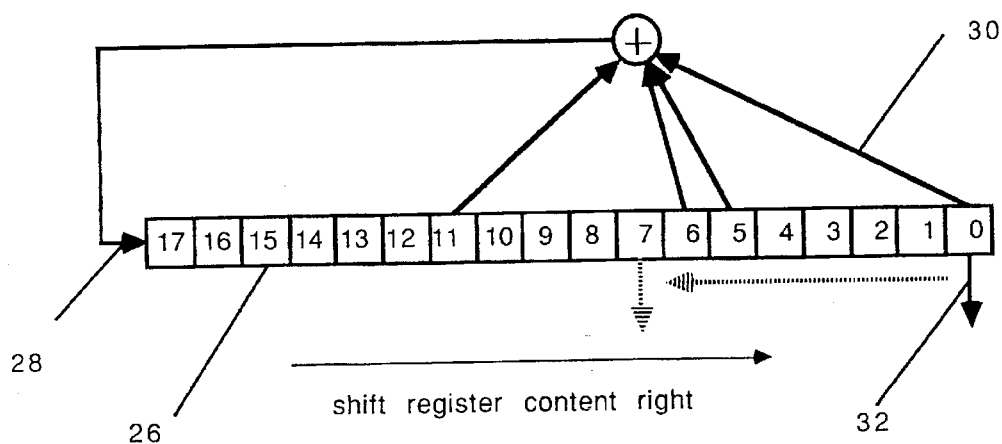
Fig. 2a --- Prior Art
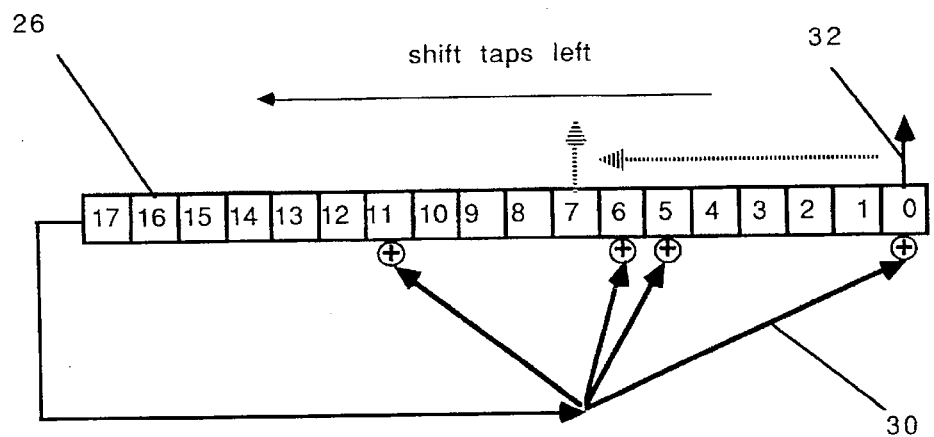
Fig. 2b --- Prior Art

VIDEO CIRCUIT FOR GENERATING SPECIAL FAST DYNAMIC DISPLAYS

GOVERNMENT CONTRACT

The U.S. government has rights in the claimed invention pursuant to NIH Grant EY-6861.

CROSS-REFERENCE TO RELATED APPLICATION

The invention of this patent is an improvement of the system of my earlier U.S. Pat. No. 4,846,567 titled "Retinal Area Response Mapping Using Simultaneous Multi-Area Stimulation with Binary M-sequences and Objective Response Mapping", granted Jul. 11, 1989.

BACKGROUND

1. Field of Invention

This invention relates to the testing of visual function, specifically to such testing by generating high speed dynamic displays for visual stimulation, followed by derivation of electrophysiological responses from such stimulation.

2. Description of Prior Art

The Multi-input M-sequence Technique Applied to Visual Evoked Responses

Early detection of retinal disease and objective evaluation of treatment require noninvasive testing of retinal function. As retinal dysfunctions commonly begin in small patches, such testing is most effective when conducted locally. When a large number of retinal areas are tested, a map of the retina can be generated with the function of each area indicated in the map.

A known method of mapping of retinal function is detailed in FIG. 1 of my above patent is schematically illustrated in FIG. 1.

As shown in FIG. 1 of that patent, a subject's eye 10 fixates on the center of an array of stimulus elements 12 on a CRT (cathode ray tube—not shown) display. These elements may be of different shapes or sizes. Typically an array of densely packed hexagons or squares is used.

All the elements are concurrently but independently modulated in time by a computer 14. Each element thus stimulates a corresponding area on a retina 16 of the subject. This visual stimulus generates or evokes bio-electrical responses in the retinal layers.

This evoked signal can be detected on the cornea of the eye by means of a special electrode 18. Such electrodes may consist of a thin conducting fiber or gold foil placed under the lower lid or a metal ring (not shown) surrounding a contact lens (not shown) covering the cornea which is not shown, but is directly under electrode 18. The response signal is amplified by an amplifier 20.

A special method of independent temporal modulation of the multiple areas permits extraction of the local responses from the response signal. The temporal modulation follows a special type of pseudo-random binary sequences, called binary m-sequences and discussed infra. This class of sequences has special properties that render it particularly useful for the purpose. The derivation and use of m-sequences is described in the next section. All areas are stimulated with the same sequence. However each element is given a different starting point in the sequence so that the contributions of all the elements to the compound response will be uncorrelated.

Local responses 22 are extracted by computation of the cross-correlation function between the applied m-sequence and the evoked response signal. The extraction is executed after completion of the recording by computer 14 by means of a special algorithm. From the array of local responses 22, a response density plot 24 is derived by means of computer 14.

This technique requires fast independent stimulation of a large number of retinal areas. Up to several hundred areas in the visual field of a human subject have to be switched rapidly and independently. The switching may be between two states differing in color, luminance level, or pattern. It has to be accomplished during retrace of the scanning electron beam of the video display. The implementation of the stimulation with conventional video techniques is difficult or impossible. In a previous implementation it was accomplished through modification of a conventional video circuit.

Binary M-sequences

Binary m-sequences are commonly generated by means of a digital shift register 26 (FIG. 2a). The modulo two sum (remainder after division by two) of the states (binary ONE or ZERO) of certain register stages is fed back to the register's serial input 28. E.g., as shown, the contents of stages 0, 5, 6, and 11 are summed modulo two and fed to the first stage. Thus, the state of the first stage will become a logic ONE if the number of logic ONEs in stages 0, 5, 6, and 11 is odd, and a logic ZERO if it is even. With proper selection of these stages (feedback taps 30), the register assumes all possible configurations (except for all ZEROs) before the process repeats itself. There are thus $2^n-1$ configurations in the cycle, where n is the number of stages in register 26. The sequence of ZEROs and ONEs derived from output stage 32 is called a binary m-sequence. Binary m-sequences are thus always of length $2^n-1$. Configurations of feedback taps that generate m-sequences can be computed or obtained from published tables.

The m-sequence can be derived from any stage of shift register 26 (FIG. 2b). A shift of output tap 32 to the left by one stage advances the sequence by one step. For a register of length n, the first n advances can be derived by moving output tap 32 to the left. Larger advances in the sequence can be obtained as the modulo two sum of specific tap configurations. FIG. 2b illustrates a mechanism for generating tap configurations for any given advance. Here the ONEs in register 26 indicate the stages of the register of FIG. 2a whose contents have to be summed (modulo two) to generate a specific advance. The process of generating taps for increasing advances starts with one output tap at the rightmost stage of the shift register. Each shift of the output tap by one stage advances the sequence by one step. This process can be continued until the tap reaches the beginning of the register. The next larger advance is produced by the parity of feedback taps 30. For subsequent advances in the sequence the entire feedback tap configuration is shifted left. Whenever a tap reaches the input stage it is replaced by the feedback tap configuration. If in this process a stage acquires two taps, then the stage always contributes even parity. Thus, this tap position is eliminated.

It follows that any advance in a binary m-sequence can be derived as the modulo two sum of certain register taps. The register taps for a specific advance are obtained by means of the operation illustrated in FIG. 2b. The register is initialized with a right justified ONE and advanced by a specified number of steps. The ONEs in the register then indicate the position of the taps for an advance of the specified number of steps.

This shift register operation can be implemented in the C-programming language by means of the following routine, called Tapregister Operation:

```
/************************************************
Tapregister Operation
*************************************************/
unsigned long Tapregister (tapconfig)
{
external unsigned long    tapwrd;         word with ones in
                                          locations of feedback
                                          taps
register unsigned long    tapregister;
register unsigned long    tapwrd;
    tapwrd      = feedbacktaps;
    tapregister = tapconfig;
    tapregister <<= 1;
    if (tapregister & test) tapregister ^ tapwrd
    tapconfig = tapregister;
    return (tapconfig)
}
/************************************************/
```

Fast Independent Modification of a Large Number of Screen Areas by Means of a Video Board with Processor A brute force solution to the fast updating of multiple screen areas makes use of a video board equipped with a special processor and a large color look-up table. In a standard pseudo-color video circuit (circuit that generates the color signal indirectly by means of a color look-up table) an address of the color look-up table (CLUT) is stored for each pixel of the display. The content of the CLUT addresses then controls a digital-to-analog converter (DAC) for the generation of the video signal. The brightness and color of a specific screen area can be modified by changing the content of a CLUT address assigned to the area. Commonly CLUTs contain up to 256 entries. This allows independent temporal modulation of up to 256 screen areas. In applications where real-time (current) data processing is needed, updating the entire CLUT during retrace of the video display takes up too much CPU (central processing unit) time. In such cases a separate, dedicated on-board processor is required.

The implementation of the dynamic stimulus with a dedicated processor requires the development of separate software for this processor. The synchronization and interplay of two processors for stimulation and data acquisition requires much labor for software development.

Fast Independent Modification of a Large Number of Screen Areas by Means of the CPU Previously I have used a single processor implementation with a pseudo-color video board and a supplementary circuit. The board featured a CLUT with 256 entries. Normally, updating of the CLUT requires 256 write operations. The supplementary circuit permits reduction of the number of such operations to eight. The circuit comprised 256 locations of memory addressed by the eight-bit video RAM (random access memory). Each location contains one-bit of information. This bit controls the most significant address bit to the CLUT. Changing this single bit thus switches a screen area between two states. High speed updating of all 256 areas is achieved by loading 32 locations of this one-bit memory in one 32-bit write operation. Each write operation thus controls 32 screen areas. Only eight write operations are required for each display frame.

This scheme is adequate for arbitrary independent temporal modulation of multiple areas between two states. However, the number of independently modulated areas is limited by the size of the CLUT (usually 256). The updating of a large number of areas during retrace of the CRT scan requires significant CPU time. This severely limits the time available for real-time processing.

Prior-art Extraction of the Binary Kernels with the M-sequence Technique

The multi-input m-sequence technique requires that different screen areas be modulated in time with the same m-sequence. A sufficient advance (channel advance or shift) is introduced between the stimulation of different areas (input channels) to render the corresponding responses uncorrelated. (For details see Sutter, E. E., A deterministic approach to nonlinear systems analysis. Chapter in: *Nonlinear Vision*. CRC Press 1992.). The contributions of each input to compound response are found on the cross-correlation cycle between the m-sequence and response cycles. The cross-correlation cycle is computed rapidly by means of the Fast M-Transform (Sutter, E. E., (1991). Fast M-Transform: Fast computation of cross-correlations with binary m-sequences. 20 SIAM *Journal on Computing*, 4.). If the responses are nonlinear, then several response components are generated for each input. All of them are found on the cross-correlation cycle. Their locations are determined by the choice of the m-sequence. In multi-input applications the procedures for localizing and extracting of specific components are complex (Sutter E. E. (1991), op. cit.).

In summary, all prior-art approaches to the rapid multi-area m-sequence stimulation with a CRT display are cumbersome and limited in the number of areas that can be stimulated.

OBJECTS AND ADVANTAGES

Accordingly several objects of my invention are: 1. To provide an improved, faster, and less expensive way to map retinal function. 2. To provide a means for reducing the computation for updating a large number of screen areas on a CRT display in accordance with a binary m-sequence to a single write operation. 3. To eliminate the need for a second processor necessary in some prior-art implementations. 4. To eliminate the development of software for such a second processor. 5. To simplify the extraction of response components from the response signal.

Several advantages of my invention are: 1. Application software is dependent on special hardware and thus better protected from illegal use. 2. The implementation of a highly complex signal analysis technique is greatly simplified.

Further objects and advantages will become apparent from a consideration of the ensuing description and the accompanying drawings.

DESCRIPTION OF DRAWINGS

FIG. 1 is a schematic representation of a prior-art system for mapping of retinal functional by means of an electroretinogram.

FIG. 2a is a schematic representation of a prior-art shift register application for the generation of binary m-sequences used in the system of FIG. 1.

FIG. 2b is a schematic representation of a prior-art shift register application for the derivation of advances in the m-sequence used in the system of FIG. 1.

Figure 3:
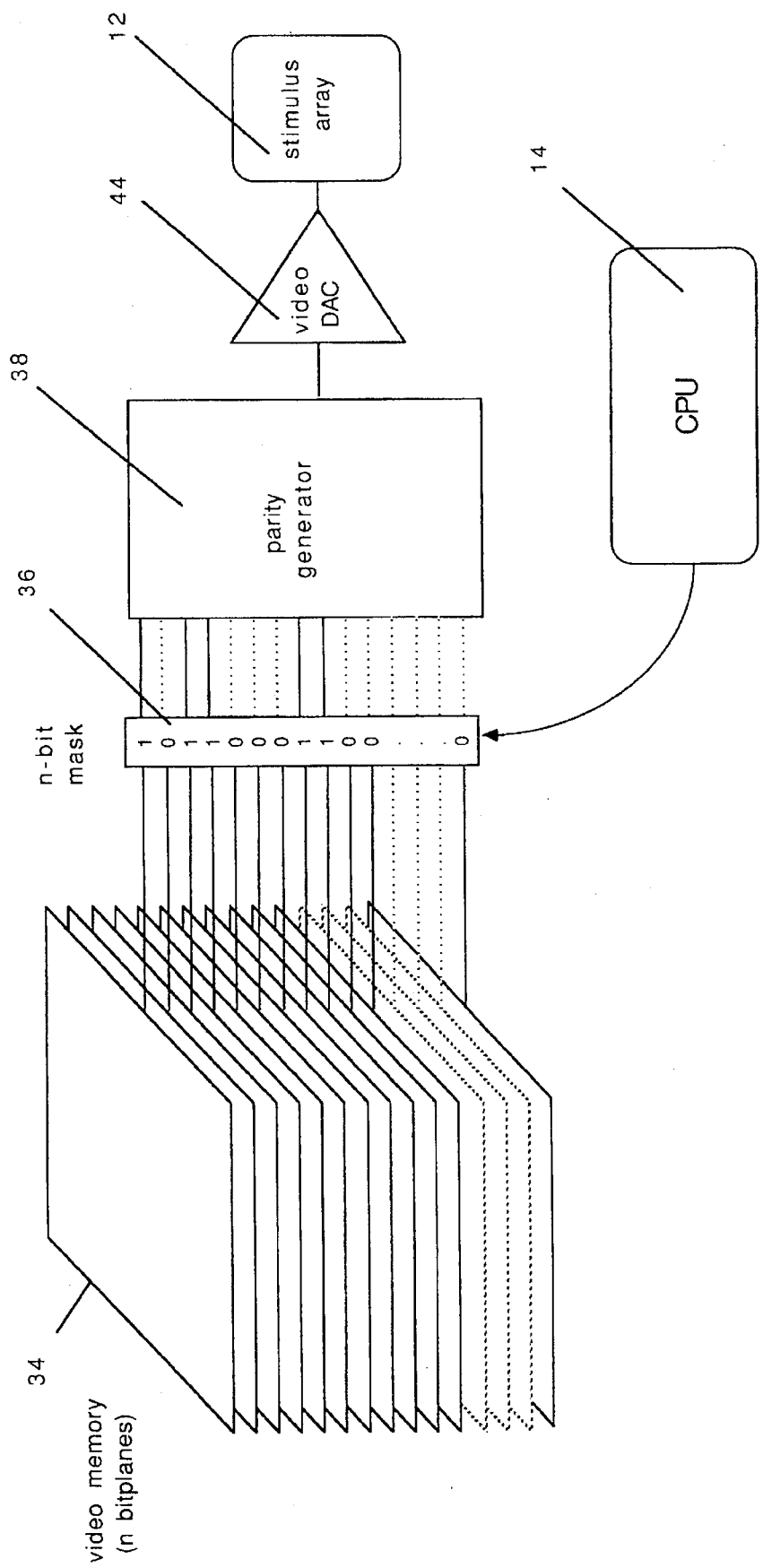
FIG. 3 is a schematic illustration of a video circuit for rapid updating of multiple screen areas in accordance with the invention.

REFERENCE NUMERALS IN DRAWINGS 10 eye of patient
12 stimulus elements or array
14 computer
16 retina
18 corneal electrode
20 amplifier
22 array of local responses
24 response density plot
26 shift register
28 serial input
30 connections to shift register stages
32 output tap
34 video memory
36 mask register
38 parity generator(s)
40 by-pass register
42 3 bit 2:1 multiplexing circuit
44 color look-up table and video digital-to-analog converters

SUMMARY

A special purpose video board permits rapid updating of a large number of areas on a CRT screen in accordance with certain classes of binary sequences called m-sequences and Walsh sequences. Special software is used to apply a video circuit to the analysis of visual responses.

DESCRIPTION OF THE VIDEO BOARD—FIG. 3

A block schematic diagram of a video board for rapid m-sequence stimulation of multiple screen areas in accordance with the invention is shown in FIG. 3. The video board is equipped with video memory 34. The memory is k bits wide, i.e., a k-bit binary word is associated with each pixel on the screen. K should be 24 bits or more. In the preferred embodiment, it was 24 bits. This video memory is organized as k 1-bit planes. Any number of these bit planes are summed modulo two (exclusive OR operation) by means of a parity generator 38. A k-bit word loaded into mask register 36 from computer 14 determines which video planes are summed. The ONEs in the register indicate the selected planes. This register is loaded from CPU 14. The output of the parity generator is connected to a digital-to-analog converter (DAC) 44. The DAC generates a video signal for stimulus array 12.

EMBODIMENT OF THE VIDEO BOARD—FIG. 4

Figure 4:
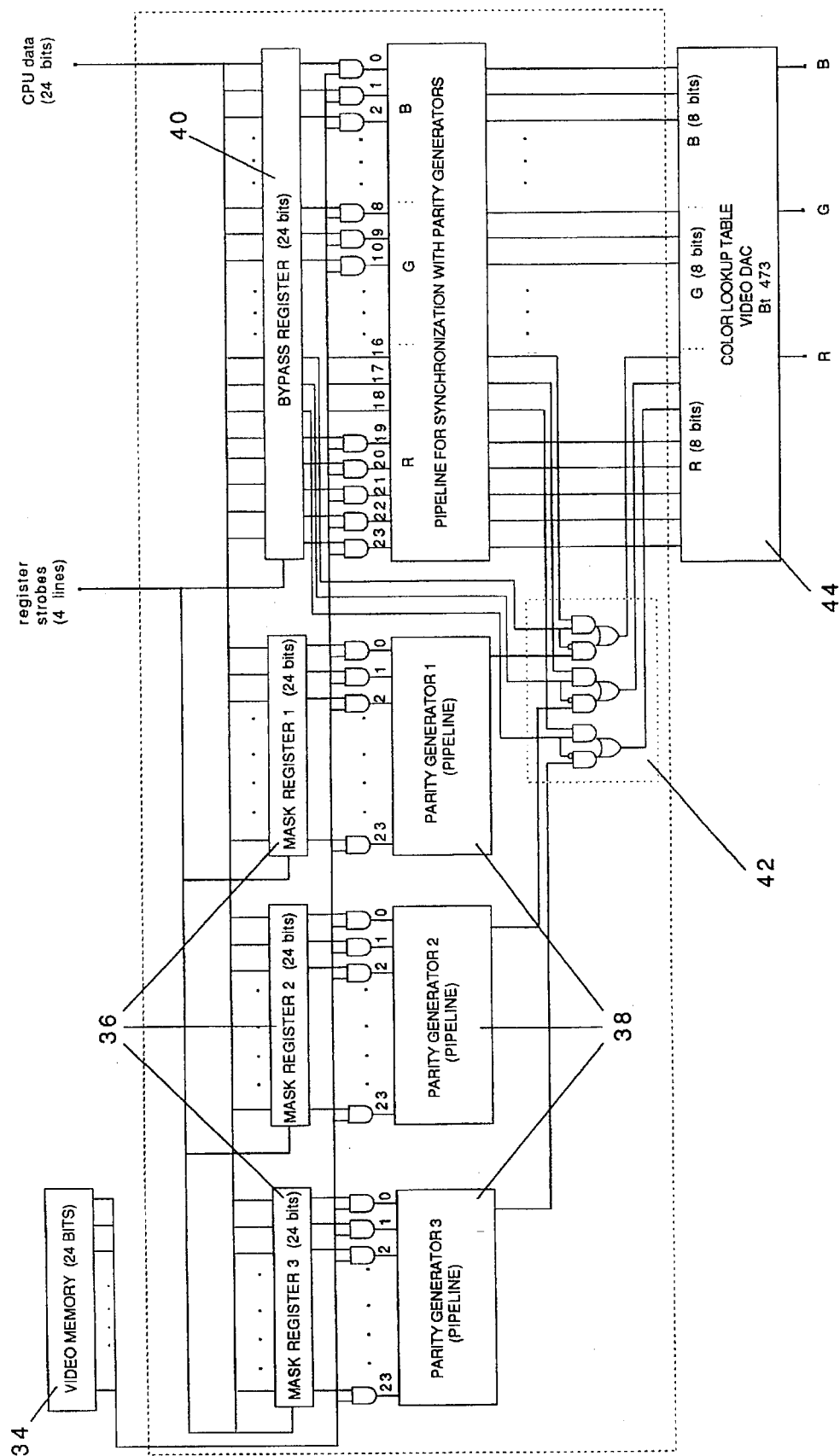
FIG. 4 is a block schematic of an embodiment of a video circuit for rapid updating of multiple screen areas in accordance with the invention.

While the simple diagram of FIG. 3 illustrates the concept of the invention, FIG. 4 shows a more detailed block schematic. It is an example of a typical embodiment of the video circuit of the invention. In this diagram, mask registers 36 for the selection of bit planes and parity generators 38 are implemented in three separate branches. The outputs of three parity generators 38 control three address bits of a color lookup table (CLUT). This CLUT is stored in RAM of a large scale integrated circuit 44 called RAMDAC. This RAMDAC also contains three digital-to-analog converters (DACs) that generate the video signal. Bypass register 40 selectively bypasses the circuit of the invention. When bypass register 40 is loaded with ONEs, mask registers 36 and parity generators 38 are bypassed to permit operation of the video board in the conventional mode. In this mode a 24-bit word is transferred from video memory 34' video DAC 44 for every pixel on the screen.

This embodiment uses a conventional RAMDAC 44 (model Bt473 made by Brooktree of San Diego, Calif.). This RAMDAC is an integrated circuit containing three CLUTs for the red, green, and blue channels of the video display. It can operate in different modes that utilize all or part of the 24 bit planes. In the 24-bit mode, bits 0 to 7, 8 to 15, and 16 to 23 are eight-bit addresses to separate look-up tables for the red, green, and blue (R, G, and B), respectively. In the eight-bit mode the addresses for all three CLUTs are controlled by the same eight bits.

When the circuit is in use, the RAMDAC is set to operate in the eight-bit mode where the eight address bits are derived from the red channel. The bypass register is loaded with ZEROs such that the input to address bits 16, 17, and 18 of the RAMDAC are derived by means of three branches of logic circuit. Each branch performs the operation illustrated in FIG. 3. In this implementation the circuit is replicated three times for control of the three address bits. In each of the three branches a mask register 36 selects a set of video bit planes. This is accomplished by a bit-wise logic AND operation between the mask register content and the 24 bit video. This operation generates a logic ONE when both input bits are logic ONEs and ZERO otherwise. The selected bit planes are summed modulo two by parity generators 38. The three outputs of the parity generators control address bits 16, 17, and 18 of the RAMDAC. The RAMDAC is operating in the eight-bit mode where the CLUT is controlled by bits 16 to 23.

OPERATION

Binary Modulation of Screen Areas

The operation is activated when bypass register 40 is cleared and the RAMDAC is set to the eight-bit mode. For binary modulation (switching of each screen area between two states) only one of the three parity generators 38 is used. Consider the use of branch 1 only. The other branches are disabled by clearing their respective mask registers (no bit planes selected). Parity generator 1 now controls bit 16, the least significant bit (LSB) of the eight-bit CLUT address. This bit is the modulo two product of the bit planes selected by the content of mask register 1. It accesses location 0 or 1 of the CLUT. These locations can be loaded with any two different colors or brightness levels.

Multi-State Modulation of Screen Areas

If two branches of parity generators 38 are used, the two parities control bit 16 and 17 of the CLUT address. The two parities thus access four different CLUT addresses (0, 1, 2, and 3). These addresses can be used in various ways. For instance, the choice of four evenly spaced levels of gray for the corresponding CLUT entries produces quaternary luminance modulation. Alternatively, four different colors can be used for chromatic stimulation.

By using all three branches of parity generators 38, it is possible to control eight different states in each screen area.

Different Modulation for Different Screen Areas

Consider the case where only one branch of parity generators 38 is used. Usually not all of the 24 video bit-planes 34 are required for the generation of the parity. Some or all of bits 17–23 can then be directly gated from the video memory to the CLUT. This is achieved by loading the corresponding bits of bypass register 40 with ONEs. These bits then determine the pair of consecutive even/odd CLUT addresses accessed through the binary modulation. Bits 17–23 of video RAM can be loaded with different values in different screen areas. This causes different even/odd address pairs to be accessed in these areas. Both levels of the binary modulation can thus be chosen independently in up to 128 different screen areas.

There are two important applications of this feature:

a) Reversal of contrast in screen areas which contain many shades of grey or hues of color. For instance, an area may contain a grating with a sinusoidal luminance profile. The binary modulation reverses the contrast of this grating.
b) Many different screen areas can be modulated independently but concurrently between different pairs of states. This capability can be used to equalize the brightness across the CRT display. Most CRT screens are afflicted by a drop-off in brightness toward the corners.

M-sequence Modulation

To achieve stimulation of separate screen areas at different advances in the m-sequence, the corresponding tap configuration is stored at each pixel. For each displayed video frame the content of shift register 26 of FIG. 2a is provided by the CPU. It is loaded as a binary word into mask register 36. At each pixel, a bit-wise logic AND operation is performed between the content of the video memory and mask register 36. Thus, the tap configurations contained in video memory determine which stages of mask register 36 are selected. Parity generator 38 then produces the modulo two sum of the selected stages. It thereby generates the modulo two sum of the corresponding bit-planes.

Consecutive configurations of shift register 26 of FIG. 2a are loaded sequentially into mask register 36. The modulo two sum generated at each pixel by parity generator 38 cycles through the m-sequence. The tap configuration stored in video memory 34 determines the relative advance in the m-sequence modulation for that pixel. The binary modulation thus produced in each screen area is used to switch between two addresses of the CLUT of RAMDAC 44. To achieve the desired optical modulation of the screen areas, these addresses are loaded with the appropriate color and brightness.

From the above it follows:

1. The number of bit planes in video memory required for the stimulation is equal to the power of the m-sequence (n for an m-sequence of length $2^n-1$).
2. The maximal number of areas whose m-sequence stimulation is different is $2^n-1$. It is reached when the relative advances between different areas becomes 1. Within this limit the operation of the device during stimulation is independent of the number of stimulated areas.
3. The relative advances in the stimulation of different areas are determined solely by the content of the video memory which is initialized before stimulation begins.
4. The maximal length of m-sequences that can be derived by means of this circuit is determined by the depth of the video memory. Modern video board designs commonly use at least 24 bits/pixel. This design thus permits the generation of m-sequence cycles of up to $2^{24}-1$ frames.

Generation of Bit Map for New Video Board Design

In preparation for the dynamic stimulation with an m-sequence of length $2^n-1$, n bit planes of video RAM 1 have to be initialized. Each screen area must be loaded with the tap configuration for the required m-sequence advance. In general it is desirable to have the advances equally spaced around the m-sequence cycle. I.e., if the number of stimulated areas is k, then the advance in the sequence from each one to the next may be chosen as 1/k cycle.

Tap configurations for specific advances can be computed as follows: Shift register 26 of FIG. 2b is initialized with a right justified ONE (least significant bit set) which corresponds to an advance of zero steps in the m-sequence. The register is then advanced by the desired number of steps. However, when the advances are large, a much faster method of computation is possible. The C-code subroutine below is an implementation of the fast technique:

Generation of Tap Configuration for Specific Advances in the M-sequence

The following C-code is a function that returns the tap configuration for a specific advance in m-sequence steps (advance) in the m-sequence.

```
/************************************************************/
unsigned long TapAdvance (unsigned long advance)
{
static unsigned long, regA, tapadvance;
    regA      = 1L;
    tapadvance = 1L;
    while (advance)
    {
        regA = Combine(regA, regA);
        if (advance & 0x1)
            tapadvance = Combine(tapadvance, regA);
        advance >> 1;
    }
return (tapadvance);
}
/************************************************************/
/************************************************************/
unsigned long Combine (unsigned long regA, unsigned long regB)
{
unsigned long regC
while (regA)
{
    if(regA & 0x1)
        regC ^= nmseq
        regB ^= tapw;
    regA >>= 1;
}
return regC;
}
/************************************************************/
```

M-sequence Stimulation of Multiple Screen Areas

The generation of consecutive configurations of the mask register for m-sequence stimulation is very rapid. It is easily implemented in real time by means of the following C-code subroutine:

```
/************************************************************/
unsigned long GenReg
static long, tapreg, genreg, tapwrd;
tapwrd;              // tap configuration for specified m-sequence
nmseq = 1L <<=n;     //length of m-sequence +1
{
    tapreg <<=1;
    if (tapreg & nmseq)
    {
        tapreg ^= tapwrd;
        genreg ^= nmseq;
    }
    tapreg <<=1;
    genreg >>=1;
return (genreg)
}
/************************************************************/
```

Derivation of the Response Components Associated with each Screen Area.

An important application of the device involves multi-input nonlinear analysis of bio-electrical responses from the retina and the visual cortex. The video circuit is used to stimulate multiple areas of the retina with binary m-sequences with different advances. A single bio-electrical response is derived from the eye or the scalp over the visual cortex. The m-sequence stimulation permits easy extraction of contributions from each stimulated area. The device greatly simplifies not only the stimulation, but also the extraction of these responses contributions.

The first step consists in computing the cross-correlation function between the m-sequence and the response cycles. This computation can be executed rapidly by means of the Fast M-Transform (Sutter, E. E. (1991), op. cit.). The computation can be further accelerated if the data are not stored in the usual, time sequential way. Instead each data point is stored at the array address specified by the configuration of the generating register. This address is thus the same n-bit word that is written to mask register 36 of the video board. If the data points are stored in this fashion the Fast M-Transform is reduced to a Fast Walsh Transform (Sutter, E. E. (1991), op. cit.).

After the response to a full stimulation cycle has been recorded, a Fast Walsh Transform is executed on the data array. The response components corresponding to different screen areas can then be read directly from the transformed array as follows:

1. First order response. This is the only non-vanishing component if the response is linear. If the response is nonlinear, this component represents a linear approximation to the response. For a particular screen area, the starting address of this component is equal to the tap configuration loaded in this area of video memory. To derive the addresses for subsequent points of the first order waveforms, the starting address is first loaded into the a register of the CPU that performs the function of shift register 26 of FIG. 2b. This function can be executed by above C-code Tapregister Operation.

Subsequent addresses are obtained by advancing of the register, step by step. The register content generated with each step is the array address for the next point of the waveform.

2. Higher order response components: These contributions to the response from nonlinearities are interactions between two or more stimulus events (second and higher order kernels). E.g., the first slice of the second order kernel is a waveform that represents the interaction between events in two consecutive time intervals. These interactions are encoded in a binary word where the ONEs represent the interacting events. In this encoding the first order response is represented by a single ONE in the least significant bit position: . . . 00001. The first slice of the second order kernel which is the effect of the response by an event in the preceding time interval is represented by the word . . . 00011. Conversely the code word . . . 001011 represents the interaction between three stimulus events spanning four time intervals. It is called a slice of the third order kernel.

In the case of multi-area stimulation by means of the video circuit the starting address of a specific kernel slice for a specific area is derived as follows: The code word for the kernel slice is combined with the content of video memory in this area by means of the above C-function Combine. Subsequent addresses are derived by means of the C-function Tapregister.

CONCLUSION, RAMIFICATIONS, AND SCOPE OF INVENTION

The reader will thus see that the video board design provides an improved and faster method for testing and mapping local retinal function. It provides a highly versatile means for the generation of multi-area m-sequence stimulation necessary for such mapping. It minimizes the information that has to be transferred to the video board for frame updating. It frees CPU time for real-time processing. It greatly simplifies the design of complex stimulus geometries and temporal stimulation schemes. It eliminates the need for a special processor to generate such stimulation and thus also the need to develop software for such a processor.

While the above description contains many specificities, these should not be construed as limitations on the scope of the invention, but rather as an exemplification of one preferred embodiment and application thereof. Many other applications are possible, as exemplified by the following:

1. Implementation of other modes of local stimulation. The special video circuit permits many of such modes. They have the property that stimulus sequences of different areas are orthogonal (uncorrelated). A set of such sequences is called a Hadamard set. Of particular interest is the stimulation of different areas with the well known series of increasing binary temporal frequencies called Walsh functions. In this application one simply writes consecutive binary numbers to mask register 26. The modulation frequency of a given screen area is then determined by the content of the corresponding locations in video memory 34. The relationship between the content of video memory and the stimulation frequency can be derived from published materials (see, e.g., Sutter E. E. (1991), op. cit.)

2. The circuit has uses outside the field of biomedical research and clinical diagnostics. One such application concerns rehabilitation of severely disabled persons. The circuit greatly facilitates the implementation of the communication aid described in U.S. Pat. No. 4,651,145, Mar. 17, 1987, titled "Communication System for the disabled in which a Display Target is Selected by Encephalogram Response". In this application items displayed on a CRT screen are independently modulated with an m-sequence. The item (field or icon) that is selected by the subject's gaze is then identified from the subject's EEG signal.

3. The circuit can also be used for the easy and fast generation of static and dynamic random dot stereograms (Julesz, B. (1960), Binocular depth perception of computer-generated patterns. *Bell Systems Tech. J.*, 39: 1125–1162; Julesz, B. (1971), *Foundations of cyclopian perception.* University of Chicago Press; Julesz, B. (1977), Recent results with dynamic random-dot stereograms. SPIE 120: 30–35. In one such application two branches of the parity generators are used to address the red and the blue gun of the cathode ray tube. A separate set of bit planes in video memory 34 is addressed by each branch. For instance, the upper twelve bit planes are used to generate the modulation of the red gun and the lower twelve bits are used for the blue gun. In each section the video memory is loaded with tap configurations that generate advances in the m-sequence used for the modulation. Different advances are used for all pixels on the screen, thus, generating a pattern of random dots. In areas that correspond to different depth planes points with the same advances are found in the two sections at different horizontal displacements relative to one another. The display is viewed through spectacles with red and blue filters in front of the left and right eye, respectively. One eye thus only sees the red dots and the other the blue dots. The horizontal displacement of corresponding dots seen by the two eyes determines the depth in space at which the dots are perceived. A static random dot stereogram is generated by writing the same binary word into the upper and lower 12 bits of the mask registers that correspond to the two parity generators used in this application. If these words are updated between frames, a dynamic random dot stereogram is generated.

4. The circuit and method of the invention permits easy and rapid multiplication of a multiplicity of binary displays of arbitrary geometry and thus presents a versatile tool for the generation of dynamic patterns and visual effects.

Accordingly, the scope of the invention should not be determined by the embodiment and specific use illustrated, but by the appended claims and their legal equivalents.

I claim:

1. A circuit for rapidly generating sequences of $2^n$ different video flames on a display having a predetermined number of pixels, comprising:

a video memory which is able to store k bits of video data for every pixel on said display, where k is an integer, and a circuit for generating the parity of a specified subset of said k bits of video data, said circuit comprising:

a k-stage binary register mask register having k outputs, one for each stage of said register, where said outputs are arranged to supply a k-bit binary signal, a circuit providing, for each pixel on said display, a bit-wise logic AND function between said k-bit binary signal and said k bits of video data, a parity generator for deriving a parity signal from the result of said bit-wise logic AND function, and a pixel means for controlling said pixels of said display according to said parity signal.

2. The circuit of claim 1 wherein said pixel means for controlling said pixels of said display comprises a switching circuit controlled by said parity signal, said switching circuit being arranged to select, in response to said parity signal, one of two predetermined voltage levels for said pixels of said display, said voltage levels being selected to determine the brightness of said pixels of said display.

3. The circuit of claim 1, further including at least one additional circuit for generating the parity of a specified subset of said k bits of binary data, each additional circuit comprising:

a mask register having k outputs, one for each stage of said register, where each output is arranged to supply a binary signal, a logic circuit providing, for each pixel on said display, a bit-wise logic AND function between said k-bit binary signal and said k bits of video data, a parity generator for deriving a parity signal from the result of said bit-wise logic AND function, said logic circuit further including a parity register combining the output of said parity generators into a binary parity word, said pixel means comprising:

a look-up table memory addressed by said parity word, and a means for controlling the state of said pixels according to the content of said look-up table memory.

4. The circuit of claim 3 wherein said pixel means is a digital-to-analog converter.

5. The circuit of claim 3, further including a bypass circuit for bypassing said parity generators for permitting direct control of said means for controlling said pixels of said display by a predetermined subset of bits of said k-bits of video data, said bypass circuit comprising:

a k-bit binary bypass register having k outputs, one for each stage of said register, where each output is arranged to supply a k-bit bypass signal, a logic circuit providing, for each pixel on said display, a bit-wise logic AND function between said bypass signal and said video data, a register combining the outputs of said bit-wise logic AND function with said parity word to form a combined binary word, said pixel means being responsive to said binary word.

6. The circuit of claim 3, further including a control circuit for selecting whether a predetermined bit in the address of said look-up table memory is controlled by a predetermined bit of said parity word or a predetermined bit of said k-bit video data, said control circuit comprising a two-to-one binary multiplexer for each bit position of said parity word, each multiplexer having two data inputs, one data output, and one control input, and wherein:

a bit position of a bypass register is connected to said control input for selecting which signal of said two data inputs is transferred to said data output, a bit of said parity word register is supplied to one of said data inputs, and a bit of said k-bit video data is supplied to the other one of said data inputs.

7. The circuit of claim 6 wherein said control circuit comprising said two-to-one binary multiplexer occurs three times.

8. The circuit of claim 7 wherein said look-up table memory has an eight-bit address and each one of said multiplexers controls one bit of said eight-bit address.

9. A method for generating fast temporal modulation of an arbitrary number of screen areas on a video display in accordance with a plurality of mutually orthogonal binary sequences belonging to a Hadamard set, each of said binary sequences of said Hadamard set being defined by the series of parities of the bitwise logic AND between a complete non-repetitive sequence of binary words of a predetermined length and a fixed binary word of said predetermined length, said method comprising:

providing a video memory which is able to store k bits of video data for every pixel on said video display, where k is an integer, initializing each of said screen areas by loading the corresponding locations in said video memory with said fixed binary word of said predetermined length, fixed binary word of said predetermined length defining one of said binary sequences belonging to said Hadamard set, providing at least one k-stage binary mask register each having k outputs, one for each stage of said mask register, where each output is arranged to supply a binary signal, sequentially loading at least one of said mask registers between frames of said video display with said complete nonrepetitive sequence of binary words of said predetermined length, said mask registers thereby having binary ONEs and ZEROs, providing, for each one of said mask registers, a circuit generating the parity of a subset of said k bits of video data, such that said binary ONEs in said mask register specify said subset, and providing a pixel means for controlling each pixel on said video display in accordance with said pities.

10. The method of claim 9 wherein said sequences of said Hadamard set are copies of a single binary m-sequence with a relative predetermined advance in time, and further including:

loading each of said screen areas with a bit configuration of length n, where n is a positive integer, said bit configurations being selected to generate said predetermined relative advance in said binary m-sequence generated in a corresponding area of said video display, and writing a sequence of $2^n-1$ binary words of length n to said mask register between flames of said video display so that consecutive configurations of said binary words are derived by shifting said binary m-sequence one bit position at a time through said binary word of length n.

11. The method of claim 9, further including:

providing a bypass circuit for bypassing said parity generators, thus permitting direct control of said means for controlling said pixels of said video display by a predetermined subset of bits of said k-bit video data of said display, said bypass circuit comprising:

a k-bit binary bypass register having k outputs, one for each bit of said register, where each output is arranged to supply a k-bit bypass signal, a logic circuit providing, for each pixel on said display, a bit-wise logic AND function between said bypass signal and said data provided by said video memory, and a register combining the bits of said bit-wise logic AND function with said parity word to form a combined binary word, initializing a subset of bits of said bypass register with binary ONEs to effect bypass of the corresponding bits of said video data, initializing said corresponding bits of said video data in a predetermined way in each one of said screen areas, providing a look-up table memory addressed by said combined binary word, providing a circuit for controlling each pixel on said video display in accordance with the content said look-up table memory, and initializing said look-up table memory to generate a predetermined state for each value of said parity in each pixel of said display.

12. The method of claim 9 wherein three of said circuits for generating the parity of a subset of said k bits of video data are provided.

13. A circuit for rapidly generating sequences of $2^n$ different video frames on a display having a predetermined number of pixels, comprising:

a video memory which is able to store k bits of video data for every pixel on said display, where k is an integer, and a circuit for generating the parity of a specified subset of said k bits of video data, said circuit comprising:

a k-bit binary register mask register having k outputs, one for each bit of said register, where each output is arranged to supply a binary signal, a circuit providing, for each pixel on said display, a bit-wise logic AND function between said binary signal and said video data, a parity generator for deriving a parity signal from the result of said bit-wise logic AND function, and a switching circuit controlled by said parity signal, said switching circuit being arranged to select, for said pixels of said display, one of two predetermined voltage levels, said voltage levels being selected to determine the brightness of said pixels of said display.

14. The circuit of claim 13, further including at least one additional circuit for generating the parity of a specified subset of said k bits of binary data, said additional circuit comprising:

a mask register having k outputs, one for each bit of said register, where each output is arranged to supply a binary signal, a circuit providing, for each pixel on said display, a bit-wise logic AND function between said k-bit binary signal and said data provided by said output of said video memory, a parity generator for deriving a parity signal from the result of said bit-wise logic AND function, said circuit further including a register combining the ordered set of parity signals into a binary parity word, a look-up table memory addressed by said parity word, and a digital-to-analog converter for converting the binary words stored in said look-up table into analog signals for controlling the state of said pixels.

* * * * *